United States Patent [19]

Tada

[11] 4,446,861
[45] May 8, 1984

[54] METHOD AND APPARATUS FOR PURIFYING CONTAMINATION OF DENTAL CONSULTATION ROOM

[75] Inventor: Yoshikazu Tada, Tokyo, Japan

[73] Assignee: Hayashikane Shipbuilding & Engineering Co., Ltd., Yamaguchi, Japan; a part interest

[21] Appl. No.: 408,568

[22] Filed: Aug. 16, 1982

[30] Foreign Application Priority Data

Sep. 4, 1981 [JP] Japan ................................ 56-138535

[51] Int. Cl.³ .......................... A62B 7/02; A61C 19/00
[52] U.S. Cl. .................................... 128/139; 128/910; 98/115 LH
[58] Field of Search .................... 128/910, 139, 1 R; 15/314, 340; 98/115 R, 115 LH; 55/419

[56] References Cited

U.S. PATENT DOCUMENTS

| | | | |
|---|---|---|---|
| 3,150,404 | 9/1964 | Johnson | 15/340 |
| 3,537,447 | 11/1970 | Gauthier et al. | 128/910 |
| 3,625,207 | 12/1971 | Agnew | 128/910 |
| 4,055,173 | 10/1977 | Knab | 128/910 |
| 4,082,092 | 4/1978 | Foster | 128/910 |
| 4,318,337 | 3/1982 | Wichmann et al. | 98/115 R |

Primary Examiner—Henry J. Recla
Attorney, Agent, or Firm—Blum, Kaplan, Friedman, Silberman & Beran

[57] ABSTRACT

A method of purifying the contamination of a dental consultation room is disclosed. The purification method is characterized in that an anesthetic gas such as laughing gas and the dust generated by drilling a tooth or false tooth of the patient are changeably sucked either from a region close to the floor of the dental consultation room, or from outside the oral cavity of the patient, and are discharged outside the consultation room. Disclosed also is an apparatus for practicing the purification method.

6 Claims, 4 Drawing Figures

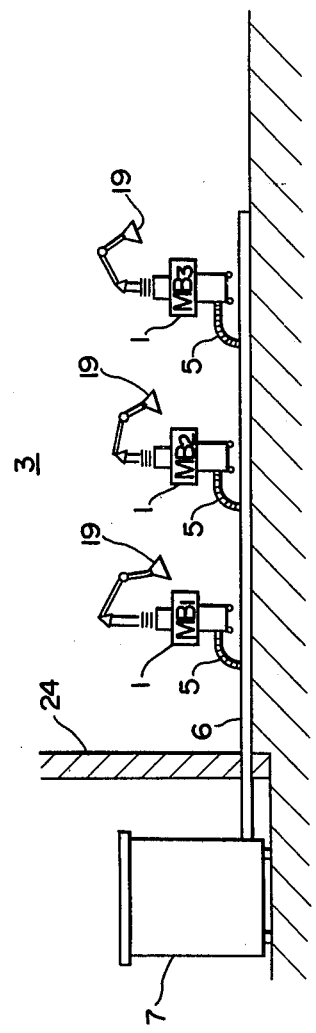
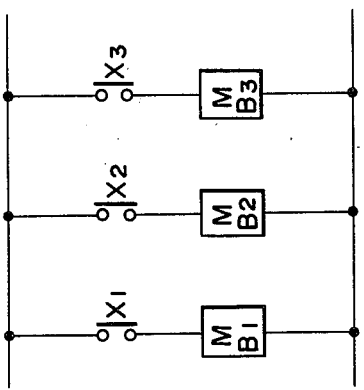
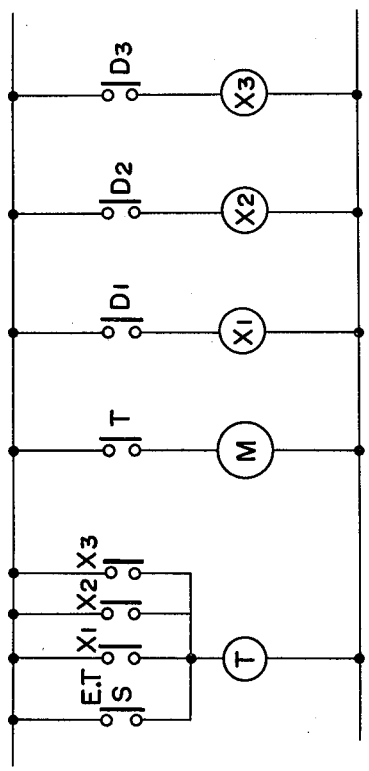
FIG. 3
FIG. 4A
FIG. 4B

METHOD AND APPARATUS FOR PURIFYING CONTAMINATION OF DENTAL CONSULTATION ROOM

BACKGROUND OF THE INVENTION

This invention relates to a method and apparatus for purifying the contamination of a dental consultation room.

Laughing gas, or rather nitrous oxide, has been used recently as an inhaled stupefacient in dental treatment, and a laughing gas sedation process has been employed especially from around 1970. The laughing gas sedation process is a process for reducing the mental and physical distress and pain of the patient during dental treatment by causing the patient to inhale a low concentration of laughing gas so that the treatment can be carried out in cooperation with the patient who is in a related state. When the patient inhales a 20 to 30% concentration of laughing gas, he does not lose consciousness but feels only slight pain and has no anxiety and hence tooth extraction can be made easier than before.

Though laughing gas is believed to have low toxicity and less side effects in comparison with other anesthetics, various problems have occured as the laughing gas sedation process has become widespread. It has been reported that since persons working in dental consultation rooms, such as the dentist, inhale laughing gas, even if its concentration is low, for an extended period of time, the occurrence of disorders such as natural abortion, renal diseases, cancer, antenatal deformities and the like in female workers in the dental consulation room is 1.3 to 2 times that of those who do not inhale anesthetic gases such as laughing gas and the occurrence of heptal diseases in male workers is 1.3 to 2.2 times that of male pediatricians ("Dental Review", Vol. 57, No. 7, June, 1981, "On Laughing Gas Contamination in Dental Range and Health of Dental Workers").

The drilling of the teeth or false teeth of the patient is effected in the dental consulation room by the use of an air turbine engine or an electric engine so that a large quantity of dust occurs. Dust having a particle size of $1\mu$ to $5\mu$ makes up 80% of the scattered dust and dust having a particle size of $6\mu$ to $10\mu$ accounts for 20% when an air turbine engine is used, though these values change according to the cutters used. Anyway, the dust is inhaled by the workers inside the dental consulation room. Incidentally, dust having a particle size of $10\mu$ or more is caught in the throat and is discharged outside the body together with phelgm and causes no particular problems.

It has been the customary practise that the assistant to the dentist inserts a suction nozzle consisting of a thin elongated pipe into the oral cavity of the patient together with the cutter so as to vacuum suck the dust. It has been found, however, that the dust removing effect of this system is amazingly low and that dust of only up to about $5\mu$ can be sucked, and dust having a particle size of up to $5\mu$ is scattered around inside the consulation room. Presumably this results from the fact that vortex flows occur inside the oral cavity. Since dust ranging from $0.6\mu$ to $5\mu$, which is most dangerous to the workers in the dental consultation room such as the dentists, scatter in the consultation room and since bacteria are attached to the dust, the workers are highly likely to be infected with type B hepatitis virus, resulting eventually in the occurrence of hepatic induration and liver cancer. In addition, the saliva and blood of the patient scatter and contaminate the dental consultation room. (Refer to the gazette of the Japan Dental Meterial and Instrument Society, "Contamination of Consultation Room and Counter-Measures", No. 11, September, 1964 and the gazette of the Japan Oral Cavity Surgery Society, "Examination of Type B Hepatitis Virus Infection in Hokkaido", Vol. 26, No. 2, 1980.)

Though the contamination of the dental consultation room by laughing gas and dust has been examined in the past as described above, sufficient counter-measures have not yet been established, especially against laughing gas. As to the latter, a small dust collector called Spotmatic (tradename) has sometimes been installed inside the consultation room but it can not discharge anesthetic gas from inside the consultation room to the outside.

SUMMARY OF THE INVENTION

With the background described above, the present invention is directed to provide a method and apparatus for rigorously purifying the contamination of a dental consultation room by sufficiently removing anesthetic gases such as laughing gas and dust generated by the drilling of the teeth of the patients that causes the contamination of the consultation room.

The method of purifying the contamination of a dental consultation room in accordance with the present invention is characterized in that anesthetic gas and dust are sucked changeably either from a region close to the floor of the dental consultation room or from outside the oral cavity of the patient and are discharged outside the consultation room.

BRIEF DESCRIPTION OF THE DRAWINGS

FIG. 3 is a schematic view showing the arrangement of a plurality of the apparatuses in accordance with the present invention; and FIGS. 4A and 4B are electric control diagrams of the apparatuses shown in FIG. 3.

DESCRIPTION OF THE PREFERRED EMBODIMENTS

Hereinafter, one embodiment of the present invention will be described with reference to the accompanying drawings.

Figure 1:
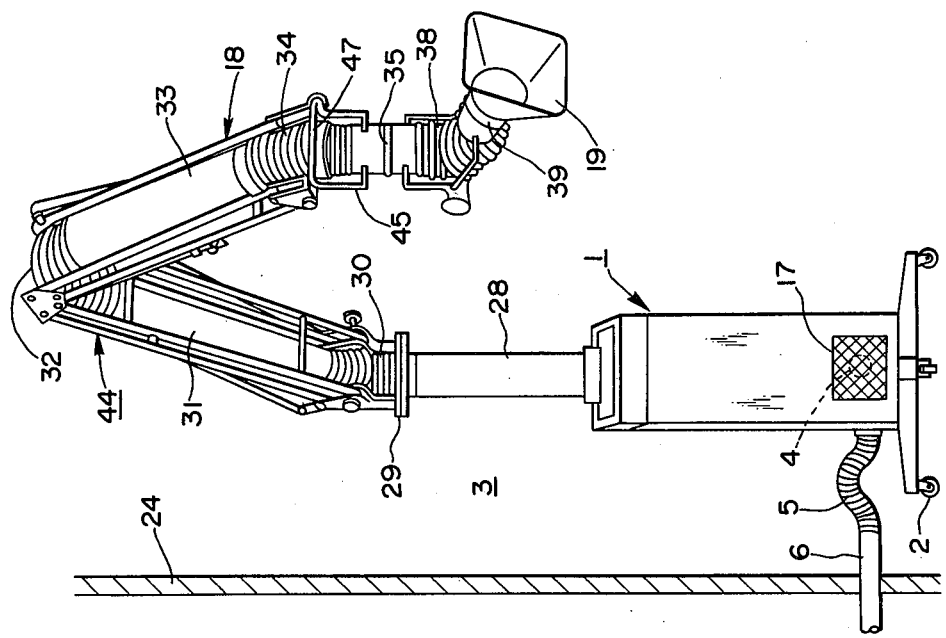
FIG. 1 is a perspective view diagrammatically showing the contamination purification apparatus of a dental consultation room in accordance with an embodiment of the present invention.
Figure 1:
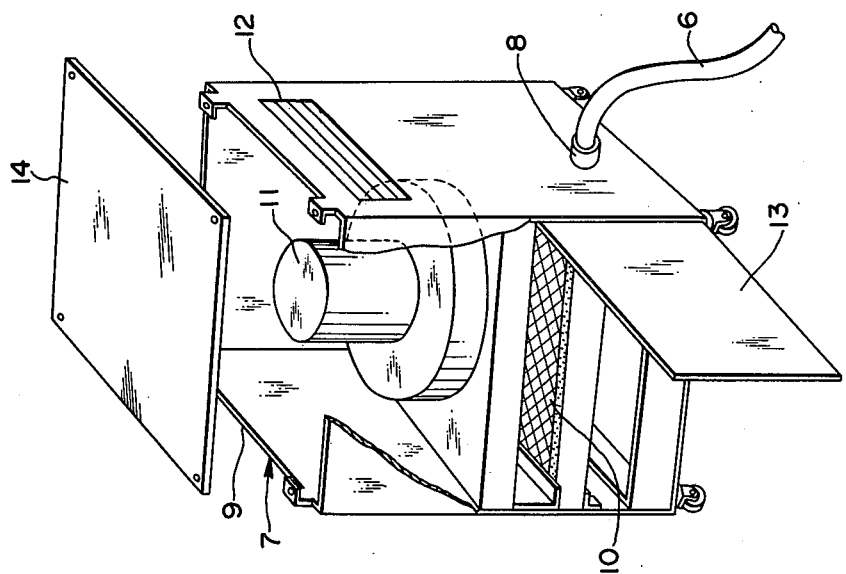
Figure 2:
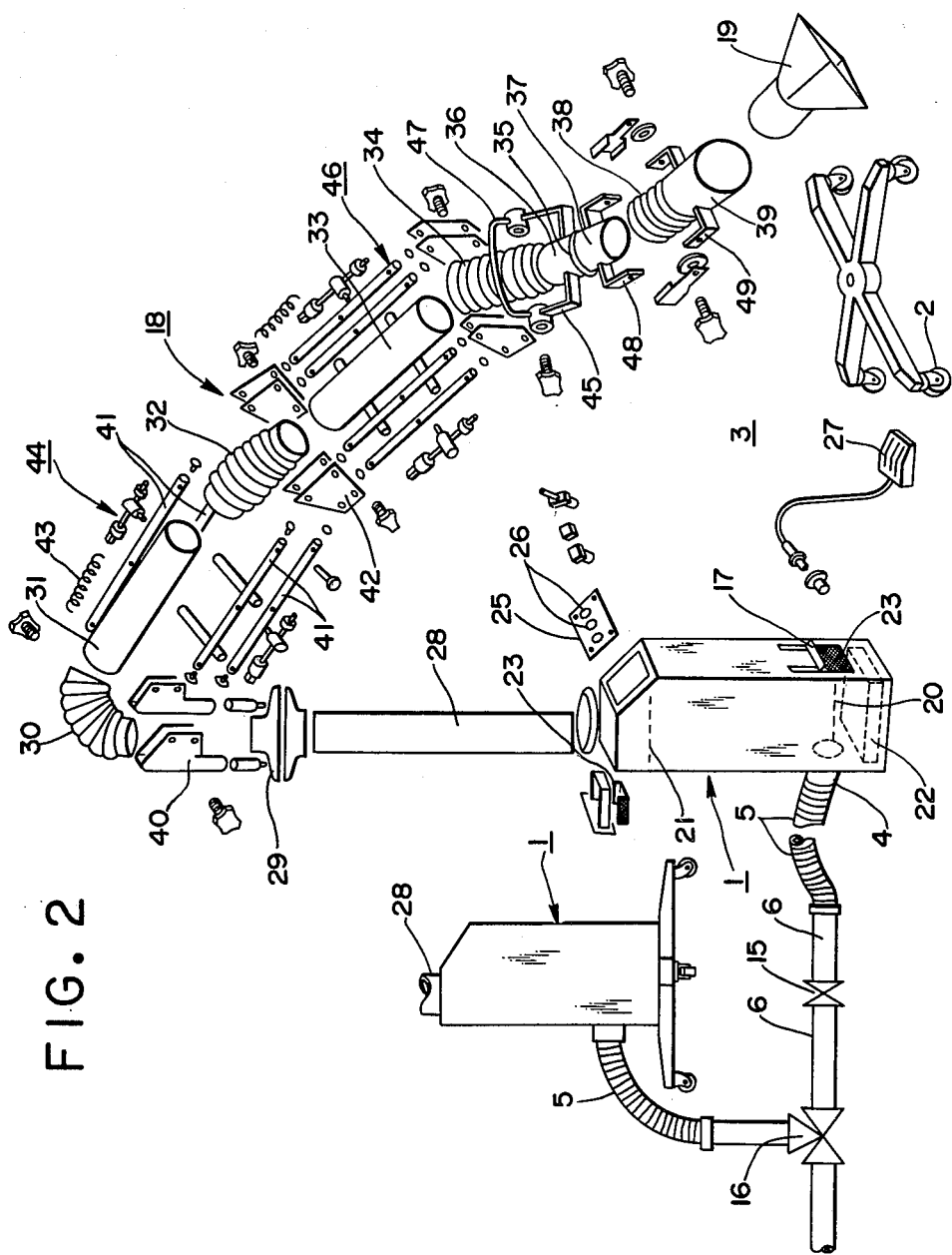
FIG. 2 is a perspective view showing the exploded relationship between the same parts.

In FIGS. 1 and 2, reference number 1 represents a stand which is shaped in a substantially box-like form and casters 2 are fitted to the lower part of the stand so that the stand can move inside a dental consultation room 3. A suction port 4 in the stand 1 communicates with the outside of the consultation room 3, that is, with a suction port 8 in a suction/dust collector 7 disposed outside a separating wall 24, via a duct 6 having a bellows-like flexible pipe 5 at a part thereof.

The suction port 8 of the dust collector 7 communicates with the suction side of a blower 11 via a filter 10 disposed inside a casing 9 and the discharger side of the blower 11 communicates with an exhaust port 12 formed in the casing 9. Reference number 13 represents a door for maintenance and inspection, disposed in the casing 9. Reference number 14 represents the upper surface cover of the casing while reference numbers 15 and 16 represent valves that are disposed in the duct 6.

An opening 17 is defined at the lower part of the stand 1 close to the floor of the consultation room 3, and the upper part of the stand 1 communicates with a suction hood 19 via a duct member 18 that will be described later. Dampers 20 and 21 are disposed inside the stand so as to changeably control the communication between the suction/dust collector 7 and the opening 17 or the duct member 18. A weight 22 is disposed at the bottom of the stand in order to stabilize the same. A control panel 25 is disposed on one side of the upper part of the stand 1 and when the switches 26 on the control panel 25 are manipulated, the blower 11 of the suction/dust collector 7 is actuated or stopped. When a pedal 27 fitted to the bottom of the stand 1 is manipulated by a foot, the opening and closing of the dampers 20, 21 are changed over by electrical means (not shown).

The duct member 18 communicating the inside of the stand 1 with the suction hood 19 has the following construction. A base pipe 28 is hermetically supported on the upper end portion of the stand so as to be capable of moving up and down and a first flexible pipe 30 is hermetically connected to the upper end portion of the base pipe 28 via a first joint 29 capable of rotating in the axial direction of the base pipe 28. A first intermediate pipe 31 and a second intermediate pipe 33 are connected hermetically to the first flexible pipe 30, the latter being connected via a second flexible pipe 32. A second joint 35 is hermetically connected to the second intermediate pipe 33 via a third flexible pipe 34. The second joint 35 is equipped with a fixed pipe 36 fixed to the third flexible pipe 34 and with a movable pipe 37 hermetically and turnably connected to the fixed pipe 36 in the axial direction of the fixed pipe. The suction hood 19 is hermetically connected to the movable pipe 37 via a fourth flexible pipe 38 and a third joint 39.

A pair of supporting members 40 project from the first joint 29 and one end each of two linkage arms 41 is turnably connected to each support member 40. The other end each of the linkage arms 41 is turnably connected to connecting plates 42 that are disposed on either side of the second flexible pipe 32. Each linkage arm 41 and support member 40 are connected by a tension spring 43, thus forming a first linkage mechanism 44.

A pair of arms 45 are fixed on either side of the fixed pipe 36 of the second joint 35, and a second linkage mechanism 46 having substantially the same construction as the first linkage mechanism 44 is disposed between the connecting plates 42 and the pair of arms 45. A handle 47 is mounted on the arms 45 fitted to the fixed pipe 36. A pair of arms 48 are fixed on either side of the movable pipe 37 of the second joint 35 while another pair of arms 49 are fixed on either side of the third joint 39. These arms 48 and 49 are pivotally fitted on either side of the fourth flexible pipe 38. The first, second, third and fourth flexible pipes 30, 32, 34, 38 have a bellows-like construction.

Nets 23 are spread at the opening 17 of the stand 1 and the lower end of the base pipe 28 of the duct member 18.

The contamination of the dental consulation room can be purified by using the contamination purification apparatus having the above-described construction in the following manner. First, when the blower 11 of the suction/dust collector 7 is actuated, the pressure in the interior of the stand 1 is reduced via the duct 6. Hence, the anesthetic gases such as nitrous oxide that stay near the floor of the consultation room 3 due to the difference of its specific gravity from air and the dust generated by drilling the teeth or false teeth of the patient and scattered inside the consultation room 3 can be sucked and removed from the opening 17 of the stand 1. When a person inside the consulation room such as the dentist steps on the pedal 27, the dampers 20 and 21 are changed over and the suction hood 19 communicates with the stand 1 via the duct member 18, whereby the anesthetic gases such as nitrous oxide and the dust can be effectively sucked and removed from outside the oral cavity of the patient immediately after they scatter into the consultation room 3.

In this case, the duct member 18 from the first to the fourth flexible pipes 30, 32, 34, 38 and its portion ranging from the first joint 29 to the suction hood 19 can be rotated around the pipe 28 while the base pipe 28 can move up and down. The duct member 18 can also be bent at a suitable angle by use of the first and second linkage mechanisms 44 and 45. The section of the duct member 18 towards the suction hood 19 end can be rotated around the fixed pipe 36 of the second joint 35, and the suction hood 19 section can be likewise bent from the second joint 35. Accordingly, the suction hood 19 can be brought to a position where the anesthetic gas and duct can be sucked and removed most efficiently within a range in which the examination and treatment of the patient is not hindered, by operating the hood 19 by the handle 47 that is fitted to the second joint 35.

The anesthetic gas and dust sucked into the stand 1 from the suction hood 19 are led into the casing 9 of the suction/dust collector 7 through the duct 6 and after the dust is collected by the filter 10, the air and anesthetic gas are expelled from the exhaust port outside the consultation room 3.

When the anesthetic gas and dust are sucked into the stand 1 from the aforementioned opening 17, they are expelled and treated in the same way as when they are sucked through the suction hood 19.

In this embodiment, the stand 1 can be moved to a suitable position inside the consultation room 3 by means of the casters 2, whenever necessary.

If the capacity of the suction/dust collector 7 is increased in advance as shown in FIGS. 4A and 4B, two or more apparatuses having the same construction as described above in the sections ranging from the bellows-like flexible pipe 5 to the side of the suction hood 19 via the valve 16 can be disposed inside the consultation room 3.

In the present invention, the mechanism for changing over and controlling the communication between the opening 17 of the stand and the suction hood 19 on the side of the suction/dust collector 7 is not limited to the dampers 20 and 21. A three-way valve may be used, for example. At times, such an arrangement may also be employed in which suction is possible from both sides of the opening and the suction hood.

In the present invention, change-over control of the suction between the opening of the stand and the suction hood is not limited to a step-type pedal in particular. Control may be effected by disposing a switch on the control panel 25 or on the handle 47 of the duct member 18, or a pedal and switch may be used in combination. It is preferable that means for adsorbing the anesthetic gases such as nitrous oxide by use of an adsorbent be disposed inside the suction/dust collector 7.

As described in the foregoing, the contamination purification apparatus in accordance with the present invention can suck and remove anesthetic gas and the dust generated by drilling of the teeth or false teeth of the patient that scatter inside the consultation room from the oral cavity of the patient. Furthermore, the apparatus of the invention makes it possible to suck and remove anesthetic gases having a greater specific gravity than air such as nitrous oxide and the dust that can not be collected by the abovementioned suction which stays close to the floor of the consultation room, where their concentrations tend to increase, and discharge them outside the consultation room. Accordingly, the apparatus of the present invention can now purify the contaminations of the consultation room by anesthetic gas that has not been accomplished in the past, and also removes dust sufficiently. Thus, the adverse influences of anesthetic gas and dust upon the workers in the dental consultation room, especially those of anesthetic gas, can be eliminated.

The contamination purification apparatus of the present invention is suitable for practising the aforementioned contamination purification method. Since the apparatus is equipped with means for changing over and controlling the suction from a suction port and from an opening of the stand, the anesthetic gas and dust inside the dental consultation room can be removed and discharged sufficiently and efficiently by use of a suction/dust collector having a relatively small capacity.

What is claimed is:

1. A method of purifying the contamination of a dental consultation room comprising the steps of selectively effecting suction of anesthetic gas and dust from a region close to the floor of the dental consultation room and from outside the oral cavity of a patient, and discharging said anesthetic gas and dust outside the consultation room, said suction being effected from a region close to the floor of the dental consultation room through an opening of a stand installed inside the dental consultation room, and from outside the oral cavity of the patient through a suction hood communicated with said stand.

2. The method of purifying the contamination of a dental consultation room as defined in claim 1 wherein suction from a region close to the floor of the dental consultation room and suction from outside the oral cavity of the patient can be controlled selectively.

3. An apparatus for purifying the contamination of a dental consultation room comprising: a suction/dust collector adapted to be installed outside said dental consultation room; a stand having a duct adapted to be installed inside said consultation room and communicated with said suction/dust collector by means of said duct; an opening proximate the bottom of said stand for sucking anesthetic gas and dust; a duct member in communication with said duct; a suction hood for sucking anesthetic gas and dust from outside the oral cavity of a patient, communicating with said stand by means of said duct member; and means for selectively controlling the communication of said suction hood and said opening of said stand with said suction/dust collector.

4. The apparatus for purifying the contamination of a dental consultation room as defined in claim 3 wherein universal joints are disposed at least between the duct member communicating said stand with said suction hood.

5. The apparatus for purifying the contamination of a dental consultation room as defined in claim 4 wherein casters are disposed on said stand so as to make said stand movable.

6. The apparatus for purifying the contamination of a dental consultation room as defined in any of claims 3, 4 or 5 wherein said duct member for connecting said stand to said suction hood includes: a base pipe having an axis capable of moving up and down with respect to said stand; a first flexible pipe having a first joint connected to said base pipe by said first joint capable of rotating around the axis of said base pipe; a second flexible pipe; a first intermediate pipe disclosed between said first flexible pipe and said second flexible pipe; a third flexible pipe having an axis; a second intermediate pipe disposed between said second flexible pipe and said third flexible pipe; a second joint capable of rotating around the axis of said third flexible pipe; a fourth flexible pipe; a third joint connected to said second joint by said fourth flexible pipe so as to be bendable with respect to said second joint fixed to said suction hood; and first and second linkage mechanism disposed on either side of said first and second intermediate pipes; said first and second linkage mechanisms being connected to each other so as to be bendable with respect to each other; said first linkage mechanism being bendably connected to said first joint while said second linkage mechanism is bendably connected to said second joint.

* * * * *